United States Patent [19]

Kim

[11] 4,253,463
[45] Mar. 3, 1981

[54] METHOD OF REDUCING INFECTION UTILIZING AN INTRAVASCULAR DEVICE HAVING ANTISEPTIC METAL PORTION

[76] Inventor: Il B. Kim, 300 Briar La., Morris, Ill. 60450

[21] Appl. No.: 86,556

[22] Filed: Oct. 19, 1979

Related U.S. Application Data

[63] Continuation of Ser. No. 841,659, Oct. 13, 1977, abandoned.

[51] Int. Cl.³ ............................................. A61M 25/00
[52] U.S. Cl. .................................................... 128/348
[58] Field of Search ................ 128/214 R, 214.4, 348, 128/349, 350, 1 R

[56] References Cited

U.S. PATENT DOCUMENTS

| 3,313,299 | 4/1967 | Spademan | 128/214.4 |
| 4,106,506 | 8/1978 | Koehn et al. | 128/348 |

Primary Examiner—Robert W. Michell
Assistant Examiner—T. J. Wallen
Attorney, Agent, or Firm—Ernest S. Kettelson

[57] ABSTRACT

An intravascular device such as a catheter, having a flexible outer tubular portion or cannula and a relatively rigid inner tubular portion or stylet of metal such as stainless steel with a sharp pointed distal end protruding from the distal end of the cannula to pierce the skin and permit entry of the cannula into the vein of a patient. The opposite, or proximal, end of the cannula includes a tubular adapter or fitting to accept a corresponding tubular adapter at the proximal end of the stylet when fully inserted into the cannula. After inserting the device into a patient's vein, the stylet is withdrawn and a connecting member of a container is connected to the tubular adapter of the cannula, either for withdrawing samples of blood or for feeding an intravenous substance into the patient's vein. The flexible outer tubular member which comprises the cannula of this invention is made of a flexible plastic material such as polyethylene and includes a metal coating to present a metal surface to the tissue of the patient at the entry point of the device into the patient's skin. A metal surface at such point has been found to minimize infection. In a modification of the device, the distal or free end portion of the cannula may be of a flexible plastic material while the opposite or proximal end portion which is in contact with the patient's tissue at the entry point when the cannula is fully inserted is made of metal.

4 Claims, 5 Drawing Figures

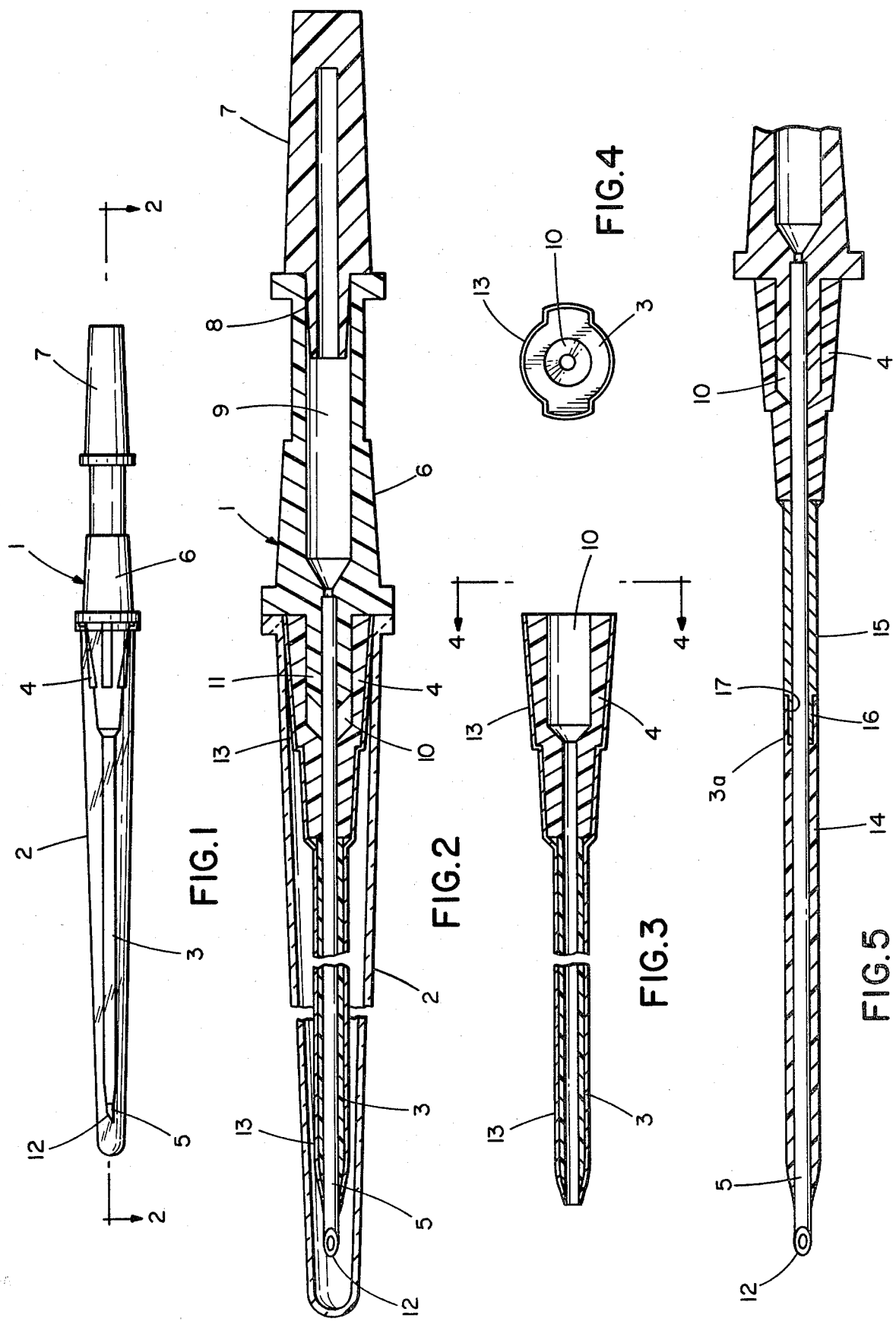

METHOD OF REDUCING INFECTION UTILIZING AN INTRAVASCULAR DEVICE HAVING ANTISEPTIC METAL PORTION

This is a continuation of application Ser. No. 841,659, filed Oct. 13, 1977, now abandoned.

BACKGROUND OF THE INVENTION

This invention relates to medical intravascular devices such as catheters for withdrawing or injecting a substance from or into a patient's vein or other channel or canal of the patient's body.

Such catheters typically comprise an elongated thin tubular member having a sharp pointed end for piercing the skin and introducing the elongated thin tubular body of the device far enough into the vein, or other internal body canal, to enable the withdrawal or injection to proceed. The tubular members of some older prior art catheters are of metal, which has the disadvantage of piercing or otherwise injuring the inner wall of the vein or other body cavity or canal in which it is inserted since the metal is stiff and does not follow the turns and bends of the vein or other body cavity or canal. To overcome this disadvantage, thin outer tubular members or cannulas of flexible plastic were provided to sheath the thin metal tubular member or stylet. The sharp pointed end of the stylet would pierce the skin and introduce the device into the vein, after which the metal stylet would be withdrawn while the flexible plastic sheath or cannula would be inserted a desired further distance into the patient's vein or other bodily portion. However, it has been found that significantly more cases of infection result at the entrance region of the body when the tissue contacting portion of the device is made of such plastic material. The present invention significantly reduces the risk of infection by coating the plastic devices with metal throughout, or at the region which is in contact with the patient's tissue at the entrance point of the device into the skin, or otherwise providing a metal contacting surface at such region.

SUMMARY OF THE INVENTION

It is an object of the invention to provide a flexible plastic intravascular device which has improved antiseptic characteristics.

It is an object of the invention to provide a flexible plastic intravascular device having an elongated thin flexible tubular sheath of plastic in which such plastic sheath is coated with metal.

It is an object of the invention to provide a flexible plastic intravascular device having an elongated thin flexible tubular sheath of which a portion extending inwardly from its free end is plastic and a portion extending inwardly from its opposite end is metal.

BRIEF DESCRIPTION OF THE DRAWING

FIG. 1 is a side elevation view of a catheter illustrating one embodiment of the intravascular medical device in accordance with this invention.

FIG. 2 is a section view taken on line 2 2 of FIG. 1.

FIG. 3 is an elevation view of the cannula sheath portion of the catheter of FIG. 1.

FIG. 4 is an end view from the right of FIG. 3.

FIG. 5 is a side elevation view of a modified catheter illustrating a second embodiment of the intravascular medical device in accordance with this invention.

DESCRIPTION OF PREFERRED EMBODIMENT

An intravascular device in accordance with this invention is illustrated in the drawing as embodied in a catheter adapted for intravenous injections. It may be embodied in any intravascular medical device having a portion that is inserted into a cavity or canal of a living body and a portion extending outwardly therefrom.

The catheter 1 described herein and illustrated in the drawing includes a protective tubular case 2 in which the device is stored when not in use. The operative parts of the catheter include a thin elongated cannula sheath 3, a female cannula adapter 4 secured to one end of the cannula sheath 3, an elongated hollow stylet 5 slidingly received through the central bore of the cannula sheath 3, and a female stylet adapter 6 secured to one end of the elongated stylet 5. A cap 7 or plug closes the open end 8 of female stylet adapter 6 to protect the stylet chamber 9 thereof until ready for use. The cap 7 is removable to permit connection of a blood sample container, or other device for either receiving blood withdrawn from a patient or infusing a substance into a patient.

The female cannula adapter 4 includes a cylindrical recess 10 in which the reduced diameter projecting end 11 of the stylet adapter 6 seats when the stylet 5 is fully received in the cannula sheath 3. When the stylet 5 is withdrawn from the cannula sheath 3, a connecting member of a blood sample container, or other device for infusing a substance into a patient or withdrawing a substance from a patient, may be connected to the cannula adapter 4 for communication through the central bore of cannula sheath 3 into a bodily cavity or canal of the patient after the cannula sheath 3 has been inserted into the patient's vein or other cavity or canal.

The elongated hollow stylet 5 is made of metal such as stainless steel, and includes a sharp pointed end 12 for piercing the patient's skin and introducing the catheter and its cannula sheath 3 into the vein or other cavity or canal of the patient. When the distal end of the cannula sheath 3 has been inserted into such vein for example, the stylet 5 may be withdrawn while the cannula sheath 3 is inserted further into the vein to a desired position for withdrawing or infusing a substance into the patient. When such position is reached, the cannula sheath 3 is secured to the patient's body in such a way that it will remain in position until the infusion or withdrawal has been completed.

The cannula sheath 3 is typically made of a flexible plastic material uch as polyethylene, to enable it to readily bend and turn with the vein or other bodily cavity or canal in which it is inserted and to avoid puncturing the wall of the blood vessel or other portion of the body. However, it has been found that increased susceptibility to infection results at the entry point into the skin of the patient when the cannula is made of flexible plastic material. Such infection does not appear to result from inability to sterilize the plastic material as well as other materials, but from the inherent characteristics and properties of the materials themselves. In accordance with this invention, the cannula sheath 3 of flexible plastic material includes a thin coating of metal 13, such as aluminum or tin foil, bonded to the outer wall of the flexible plastic sheath 3. The process of bonding a thin layer of metal to plastic is known, and illustrative processes are described in available literature including various patents such as U.S. Pat. No. 3,589,975 and the reference patents cited therein. The cannula adapter 4 may also be of flexible plastic material and may be coated with a thin coating of metal 13. While aluminum and tin foil have been mentioned, other common metals may be used such as stainless steel and any method of applying an outer layer of metal to a plastic sheath may be employed within the scope of this invention.

In accordance with a modification of this invention, the cannula sheath 3a includes a forwardly extending or distal portion 14 of flexible plastic and a rearwardly extending or proximal portion 15 of metal such as stainless steel. The proximal portion 15 of metal extends from the cannula adapter 4 to an intermediate point 16 spaced from cannula adapter 4 a sufficient distance that when the cannula 3a has been inserted into the blood vessel or other portion of a patient's body the entry point through the patient's skin will be adjacent to and in contact with the metal portion 15 of the cannula sheath 3a. The metal portion 15 includes a reduced diameter hollow projecting stud 16 at its end opposite the cannula adapter 4, received in a corresponding cylindrical recess 17 formed in the adjacent end of the flexible plastic portion 14. The projecting stud 16 is received in recess 17 in a press fit and may be cemented therein for a permanent connection.

I claim:

1. A method of reducing infection utilizing an intravenous device during a medical procedure performed on a patient wherein a substance is injected into the body of a patient or withdrawn therefrom, including the steps of connecting a flexible tubular member to a first end of a tubular member having an exterior surface of common metal, inserting said flexible tubular member wholly into the body of said patient and said metal tubular member partially into the body of said patient past said first end thereof so the portion of said intravenous device in contact with said patient's body at the insertion point is metal, and keeping said intravenous device in such position with metal in contact with said patient's body at insertion point until completion of said medical procedure.

2. A method of reducing infection utilizing an intravenous device as set forth in claim 1, wherein said step of connecting a flexible tubular member to said first end of said tubular member having an exterior surface of common metal includes the step of selecting a tubular member of stainless steel for connection of a first end thereof to said flexible tubular member.

3. A method of reducing infection utilizing an intravenous device as set forth in claim 1, wherein said step of connecting a flexible tubular member to said first end of said tubular member having an exterior surface of common metal includes the step of selecting a tubular member having an exterior surface of tin for connection of a first end thereof to said flexible tubular member.

4. A method of reducing infection utilizing an intravenous device as set forth in claim 1, wherein said step of connecting a flexible tubular member to said first end of said tubular member having an exterior surface of common metal includes the step of selecting a tubular member having an exterior surface of aluminum for connection of a first end thereof to said flexible tubular member.

* * * * *